US008877711B2

(12) United States Patent
Kiessling et al.

(10) Patent No.: US 8,877,711 B2
(45) Date of Patent: Nov. 4, 2014

(54) OCTANOATE-REDUCED HUMAN ALBUMIN

(75) Inventors: Peter Kiessling, Marburg (DE); Dietrich Bosse, Cordast (CH); Johannes Zeiss, Marburg (DE); Gaston Diderrich, Gladenbach (DE)

(73) Assignee: CSL Behring GmbH, Marburg (DE)

( * ) Notice: Subject to any disclaimer, the term of this patent is extended or adjusted under 35 U.S.C. 154(b) by 0 days.

(21) Appl. No.: 13/482,897

(22) Filed: May 29, 2012

(65) Prior Publication Data
US 2012/0238998 A1    Sep. 20, 2012

Related U.S. Application Data

(62) Division of application No. 12/086,867, filed on Jun. 20, 2008, now abandoned.

(30) Foreign Application Priority Data

Dec. 22, 2005   (DE) .......................... 10 2005 062 043

(51) Int. Cl.
| | |
|---|---|
| A61K 38/38 | (2006.01) |
| C07K 14/76 | (2006.01) |
| A61P 1/16 | (2006.01) |
| C07K 14/765 | (2006.01) |
| A61K 38/00 | (2006.01) |

(52) U.S. Cl.
CPC .............. *C07K 14/765* (2013.01); *A61K 38/00* (2013.01)
USPC ......................................... 514/15.2; 530/362

(58) Field of Classification Search
CPC .............................. A61K 38/00; C07K 14/765
See application file for complete search history.

(56) References Cited

U.S. PATENT DOCUMENTS

| | | | |
|---|---|---|---|
| 2,705,230 | A | 3/1955 | Reid |
| 4,156,681 | A | 5/1979 | Schneider et al. |
| 5,118,794 | A | 6/1992 | Grangeorge et al. |
| 5,561,115 | A | 10/1996 | Tenold |
| 5,744,042 | A * | 4/1998 | Stange et al. ................. 210/645 |
| 5,919,907 | A | 7/1999 | Shanbrom |
| 6,908,749 | B2 | 6/2005 | Nouchi et al. |
| 2006/0234907 | A1 | 10/2006 | Gehringer |
| 2008/0269124 | A1 | 10/2008 | Stange |

FOREIGN PATENT DOCUMENTS

| | | |
|---|---|---|
| AU | 2004212324 B2 | 8/2004 |
| WO | WO 00/56768 A2 | 9/2000 |
| WO | WO 2004/071524 A | 8/2004 |
| WO | WO 2004/080575 A1 | 9/2004 |
| WO | WO 2006/120226 | 11/2006 |
| WO | WO 2006/120226 A1 | 11/2006 |

OTHER PUBLICATIONS

Machined translated WO 2006/120226 A1, enclosed, pp. 1-17.*
Albumin-A-3782-Sigma-2003 document, from Sigma catalog 2002-2003, pp. 1-2.*
Albumin—*Homo sapiens*, from http://www.ncbi.nlm.nih.gov/protein/AAA98797.1, pp. 1-2, accessed Apr. 16, 2014.*
Caprylic acid—octanoate, from http://www.healthline.com/natstandardcontent/caprylic-acid, pp. 1-2, accessed Nov. 6, 2013.*
German Office Action dated Dec. 6, 2006, for German Patent Application No. 10 2005 062 043.4.
Anraku, M., et al., "Stabilizing Mechanisms in Commercial Albumin Preparations: Octanoate and N-acetyl-1-tryptophanate Protect Human Serum Albumin Against Heat and Oxidative Stress," *Biochimica et Biophysica ACTA (BBA)-Proteins & Proteomics*, Elsevier, vol. 1702, No. 1, pp. 9-17, 2004.
Chen, R.F., "Removal of Fatty Acids from Serum Albumin by Charcoal Treatment," *Journal of Biological Chemistry*, American Society of Biolochemical Biologists, vol. 242, No. 2, pp. 173-181, 1967.
Constantino, H.R., et al., "Aggregation of a Lyophilized Pharmaceutical Protein, Recombinant Human Albumin: Effect of Moisture and Stabilization by Excipients," *Bio/Technology*, Nature Publishing Co., vol. 13, No. 5, pp. 493-496, 1995.
Kragh-Hansen, U., et al., "Practical Aspects of the Ligand-Binding and Enzymatic Properties of Human Serum Albumin," *Biological and Pharmaceutical Bulletin*, vol. 25, No. 6, pp. 695-704, 2002.
Olsen, H., et al., "Pharmaceutical-Grade Albumin: Impaired Drug-Binding Capacity in Vitro," *BMC Clinical Pharmacology*, Biomed Central, London, GB, vol. 4, No. 1, p. 4, 2004.
Gentilini, P., et al., "Albumin Improves the Response to Diuretics in Patients with Cirrhosis and Ascites: Results of a Randomized, Controlled Trial," *Journal of Hepatology* 30: 639-645 (1999).
Ginès, A., et al., "Randomized Trial Comparing Albumin, Dextran 70, and Polygeline in Cirrhotic Patients with Ascites Treated by Paracentesis," *Gastroenterology* 111: 1002-1010 (1996).
Heemann, U., et al., "Albumin Dialysis in Cirrhosis with Superimposed Acute Liver Injury: A Prospective, Controlled Study," *Hepatology* 36: 949-958 (2002).
Matthes, G., et al., "Analysis of Plasma Proteins and Tumor Screening Diagnostic Using ESR," *New Drugs*, pp. 26-32 (2000).
Matthes, G., et al., "Albumin Transport Analysis of Different Collected and Processed Plasma Products by Electron Spin Resonance Spectroscopy," *Transfusion and Apheresis Science* 27: 129-135 (2002).
Sort, P., et al., "Effect of Intravenous Albumin on Renal Impairment and Mortality in Patients with Cirrhosis and Spontaneous Bacterial Peritonitis," *The New England Journal of Medicine* 341: 403-409 (1999).
Office Action mailed Apr. 15, 2011, for U.S. Appl. No. 12/086,867.
Office Action mailed Jul. 26, 2011, for U.S. Appl. No. 12/086,867.
Final Office Action mailed Dec. 28, 2011, for U.S. Appl. No. 12/086,867.

(Continued)

*Primary Examiner* — Julie Ha
*Assistant Examiner* — Li Ni Komatsu
(74) *Attorney, Agent, or Firm* — Finnegan, Henderson, Farabow, Garrett & Dunner, LLP (57) ABSTRACT

A method is described that improves the transport properties of albumin produced on an industrial scale, wherein the albumin is mixed, during the production process, with substances that saturate the binding points on the albumin. Furthermore, pasteurized and then octanoate-reduced human albumin and therapeutic uses of such albumin is described. Such albumin may be useful in detoxifying human plasma, e.g. for the intravenous treatment of acute or chronic liver diseases, and as a dialysate in extracorporeal liver dialysis.

13 Claims, 5 Drawing Sheets

(56) References Cited

OTHER PUBLICATIONS

International Search Report for PCT Application No. PCT/EP2006/011970, mailed Jun. 1, 2007.

Mitteilung gemäβ Artikel 94(3) EPÜ, dated Mar. 26, 2012, for European Patent Application No. 06 829 547.6 (7 pages).

H. R. Costantino et al., "Heterogeneity of serum albumin samples with respect to solid-state aggregation via thiol-disulfide interchange—Implications for sustained release from polymers," *Journal of Controlled Release* 44:255-261 (1997).

S. Klammt et al., "Albumin Binding Capacity (ABiC) is reduced in commercially available Human Serum Albumin preparations with stabilizers," *Z Gastroenterol.* 39:24-27 (2001).

*European Pharmacopoeia*, 5$^{th}$ Ed., p. 1731, entry 01/2005:0255 for "Human Albumin Solution," (2004).

Translation of Communication pursuant to Article 94(3) PEC (Mitteilung gemäβ Artikel 94(3) EPÜ), dated Mar. 26, 2012, for European Patent Application No. 06 829 547.6 (6 pages).

Translation of German Office Action dated Dec. 6, 2006, for German Patent Application No. 10 2005 062 043.4 (3 pages).

"Sekijuji [Red Cross] Albumin 20% I.V.: Human Serum Albumin," Marketer: Japanese Red Cross Society, Nov. 2013 (Original, 4 pages; Translation, 3 pages).

"Blood Donation Albumin 25%: [Benesi]," Marketer: Mitsubishi Tanabe Pharma, Oct. 2012 (Original, 4 pages; Translation, 4 pages).

Cohn, E.J. et al., "Preparation and Properties of Serum and Plasma Proteins," Dept. of Physical Chem., Harvard Med. School, Mar. 1946 (17 pages).

"Production Information: Albumin, Human," Sigma-Aldrich, Oct. 9, 1996 (3 pages).

Atkinson, James P., "The Fractional Precipitation of the Globulin and Albumin of Normal Horse's Serum and Diphtheria Antitoxic Serum, and the Anti-Toxic Strength of the Precipitates," Research Lab., Dept. of Health, NYC, Oct. 1, 1900 (9 pages).

Examination report issued by the Canadian Intellectual Property Office, mailed Jun. 27, 2014, for Canadian Patent App. No. 2,634,329 (3 pages).

\* cited by examiner

Fig. 2: Detoxification efficiency (DTE) Human Serum Albumin (HSA) inprocess controls Fig. 3: Mini-MARS® test setup Fig. 4: Detoxification efficiency (DTE) of Human Serum Albumin (HSA) in the dialysate circuit Fig. 5 Detoxification efficiency (DTE):
Human Serum Albumin (HSA) in the plasma pool, time point t0 (gray) and t1 (black)

OCTANOATE-REDUCED HUMAN ALBUMIN

CROSS REFERENCE TO RELATED APPLICATIONS

This application is a divisional of U.S. patent application Ser. No. 12/086,867 Jun. 20, 2008 now abandoned, which is a national stage filing under 35 U.S.C. §371 of International Application No. PCT/EP2006/011970, filed on Dec. 13, 2006, which claims the benefit of priority of German Application No. 10 2005 062 0434.4, filed Dec. 22, 2005. All of these applications are incorporated herein by reference in their entireties.

The invention relates to improvement of the transport properties of an albumin produced on an industrial scale, for example by the Cohn Process or by recombinant methods, with substances that saturate the binding sites on the albumin and therefore impair the binding and transport properties of the final product being added to the albumin in the course of its production. A special embodiment of the invention relates to pasteurized and then octanoate-reduced human albumin for therapeutic use, in particular in detoxification therapy of human plasma for example for intravenous therapy of acute or chronic liver diseases and as dialysate for extracorporeal hepatic dialysis with albumin in the MARS® system (Molecular Adsorbent Recirculating System) or in "single-pass" dialysis.

Albumin is the commonest protein in the blood plasma. It makes a significant contribution to the osmotic pressure of plasma and is therefore an important factor for regulating the volume of plasma and tissue fluid. The commonest clinical use of albumin is therefore as plasma volume expander.

Within the last 10 years, however, albumin has found increasing therapeutic use as a transport protein on account of its physiological properties.

Albumin is the principal transport protein in human plasma. It binds a broad spectrum of compounds and metabolites, for example steroids, bile acids, fatty acids and amino acids, heavy metals and pharmacological substances, for example warfarin. The substances bind primarily to two subdomains of the albumin, Sudlow I (bilirubin, warfarin) and Sudlow II (tryptophan, octanoate, fatty acids), with heavy metals mainly binding to the N-terminus (Peters et al. "All about albumin"; 1996; Academic Press).

Detoxification therapy utilizes the transport function of albumin. The main indications comprise the intravenous treatment of patients with chronic or acute liver diseases, for detoxification (e.g. hyperbilirubinemia) and for improvement of diuresis in patients with liver diseases and ascites (Gentilini et al., 1999) or in patients with nephrotic syndrome (Gines et al., 1998), as well as in combination therapy with antibiotics in patients with bacterial peritonitis (Sort et al., 2000).

In clinical therapy with MARS® (Molecular Adsorbent Recirculating System) hepatic dialysis or so-called "single-pass" dialysis, the binding of toxic metabolites (e.g. bile acids, bilirubin) or medicinal products (e.g. phenytoin) to albumin is utilized for detoxification in patients with acute or chronic liver disease. Through extracorporeal dialysis against albumin, the patient's blood is detoxified and patients' survival rate is increased significantly (Heemann et al., 1999).

In the course of many production processes, substances are added to albumin that bind to the latter and, through occupying these binding sites, also lower the binding capacity of albumin to other substances in the final product. Thus, before pasteurization for example, as a rule a stabilizer such as octanoate (caprylate) or N-acetyl-tryptophan is added to albumin, to prevent the denaturation or polymer formation of albumin during the pasteurization process. In other methods of production, which do not necessarily envisage a pasteurization step, for example in the production of recombinant albumin, octanoate for example is added in order to prevent polymer formation during storage.

Shanbrom (U.S. Pat. No. 5,919,907, priority: 22 Dec. 1997) notes that stabilizers such as octanoate occupy binding sites in pasteurized albumin, and proposes an alternative production process, which avoids the addition of octanoate, replacing the virus inactivation process of pasteurization with an iodine treatment. An albumin produced in this way is said to be especially suitable for the treatment of hyperbilirubinemia.

Gehringer (WO 2004/071524, priority 13 Feb. 2003) also points to the problem of reduction of the binding capacity of albumin by bound pasteurization stabilizers. In consequence, patients receiving infusions of albumin with its binding capacity for medicinal products reduced in this way are exposed, on administration of pharmaceutical active substances, to an appreciably increased concentration of free (i.e. not bound to albumin) active substance, which of course means that the patient has an increased risk of excessive pharmacological effects and side effects. It is therefore proposed to use an albumin for which pasteurization is replaced with the SD (solvent/detergent) method, so that by avoiding the need to add a pasteurization stabilizer, occupation of binding sites is also avoided.

Chen (JBC, 1967) notes that fatty acids, including octanoate, can be removed from albumin with activated carbon, and especially effectively at low pH, in particular pH 3-4.

Olsen et al. (BMC Clin Pharm, 2004) show that pharmaceutical albumins have a markedly reduced binding capacity for a number of medicinal products, which is attributed to occupation of binding sites of the albumin by pasteurization stabilizers such as octanoate or N-acetyl-DL-tryptophan. It was shown that after adding these stabilizers to unloaded albumin the binding capacity could be reduced to that of a pharmaceutical albumin (octanoate-loaded) and that conversely an octanoate-loaded pharmaceutical preparation of albumin could be converted by treatment with activated carbon to a form that did not differ, with respect to binding behavior, from unloaded albumin.

There is an increasing medical need for albumin in indications that make use of the transport function of albumin. Albumin can still only be produced economically on a large scale from plasma. The Cohn Process is mainly used for this. Therapeutic proteins purified from plasma must be treated with effective methods of virus inactivation, before they can be administered to humans. The oldest reliable virus inactivation process still in use, so far with no known case of infection due to a plasma preparation treated in this way, is pasteurization. Therefore a large proportion of the albumin on the market still undergoes pasteurization during its production. As stabilizers such as octanoate are added during pasteurization, albumin obtained in this way is less suitable for transport functions than stabilizer-free or stabilizer-reduced albumin, because its binding capacity is reduced by bound stabilizers. The same applies to albumin produced by other methods, which does not necessarily undergo pasteurization, for example in the production of recombinant albumin, where stabilizers such as octanoate are added in order to prevent polymer formation during storage.

The present invention therefore has the aim of providing medicinal products based on albumin for certain indications, where the mode of action of the medicinal product in the particular indications is based on the transport functions of albumin, i.e. on the binding of other substances to albumin, starting from albumin preparations to which substances were added during their production process, which occupy and therefore block the binding sites in the albumin produced in this way, with the result that the use of said albumin in the particular indications is less efficient.

A stabilizer-free or stabilizer-reduced albumin has, in the aforementioned indications, a considerably higher detoxification efficiency and binding capacity for toxins (active metabolites) than conventional albumin. The invention describes, along with the planned field of application, the production of the novel product and detection of product improvement by novel methods of analysis (analysis of the improvement of albumin transport and binding properties with ESR (electron spin resonance spectroscopy) (Matthes et al., 2000). In ESR, by loading albumin with a spin probe (e.g. 16-doxylpalmitic acid) to represent a fatty acid, the transport function and binding capacity of the albumin for fatty acids are measured in the presence of ethanol. From the ESR signal it is possible to calculate the ratio of loading capacity to unloading capacity (DTE=Detoxification efficiency (Matthes et al. 2002, Transfus Apheres Sci.)). The more firmly a substance binds to albumin, the higher the DTE ratio.

The use of stabilizer-free or stabilizer-reduced albumin in detoxification has not been described previously. By determining the transport parameters by ESR, it could be shown that in the commercial production of albumin based on the Cohn process, addition of octanoate as required in the production process causes a marked reduction in the transport properties of albumin. If the octanoate is removed from albumin produced in this way, which can be done for example by treatment with activated carbon in acid conditions, this restores the original transport properties and hence restores the detoxification efficiency of a native serum albumin.

The method is mainly suitable for the use of albumin preparations produced on a large scale, to which substances are added during their production process which occupy and hence block the binding sites in the albumin produced in this way, and when these substances are removed to the greatest possible extent the binding capacity of these albumin preparations is improved or restored, for the production of a medicinal product whose pharmacological mechanism of action depends on the binding of other substances to the albumin that is used. For example, >50%, or for example >75%, or for example >95% of the substance originally bound to albumin is removed. In particular, albumins produced in this way are suitable for the production of a medicinal product for the detoxification of human plasma.

A preferred embodiment of the invention relates to albumin preparations whose binding capacity is above that of plasma albumin. In these albumin preparations, not only the stabilizers optionally added during the production process, but also the substances that bind naturally to albumin in the plasma, have been reduced or removed completely. These albumin preparations reach DTE ratios of for example more than 100% (100%=plasma albumin), for example more than 200%, for example more than 250%.

One embodiment of the invention relates to the use of albumin preparations produced on a large scale after removal of albumin-bound pasteurization stabilizers. Preferred pasteurization stabilizers are in this case octanoate and/or N-acetyl-tryptophan.

A further embodiment of the invention relates to the use of albumin preparations produced on a large scale after removal of albumin-bound substances which prevent polymer formation of albumin, in particular the removal of octanoate.

The invention relates equally to liquid and to freeze-dried albumin preparations.

Albumin preparations according to the invention are for example administered parenterally, for example intravenously. One embodiment of the invention relates to the use of an albumin produced according to the invention in extracorporeal plasma dialysis, for example MARS ® (Molecular Adsorbent Recirculating System) dialysis or "single-pass" dialysis.

The albumin preparations produced according to the invention are suitable in particular for the production of a medicinal product for the treatment of chronic or acute liver diseases ((e.g. chronic hepatic cirrhosis with ascites, acute hepatic intoxication with encephalopathy (hepatic coma)), for detoxification of medicinal products (e.g. warfarin overdose) or metabolites (e.g. hyperbilirubinemia) and for improvement of diuresis in patients with liver diseases and ascites (Gentilini et al., 1999) or in patients with nephrotic syndrome (Gines et al., 1998), and for combination therapy with antibiotics in patients with bacterial peritonitis (Sort et al., 2000).

EXAMPLES

Example 1

Figure 1:
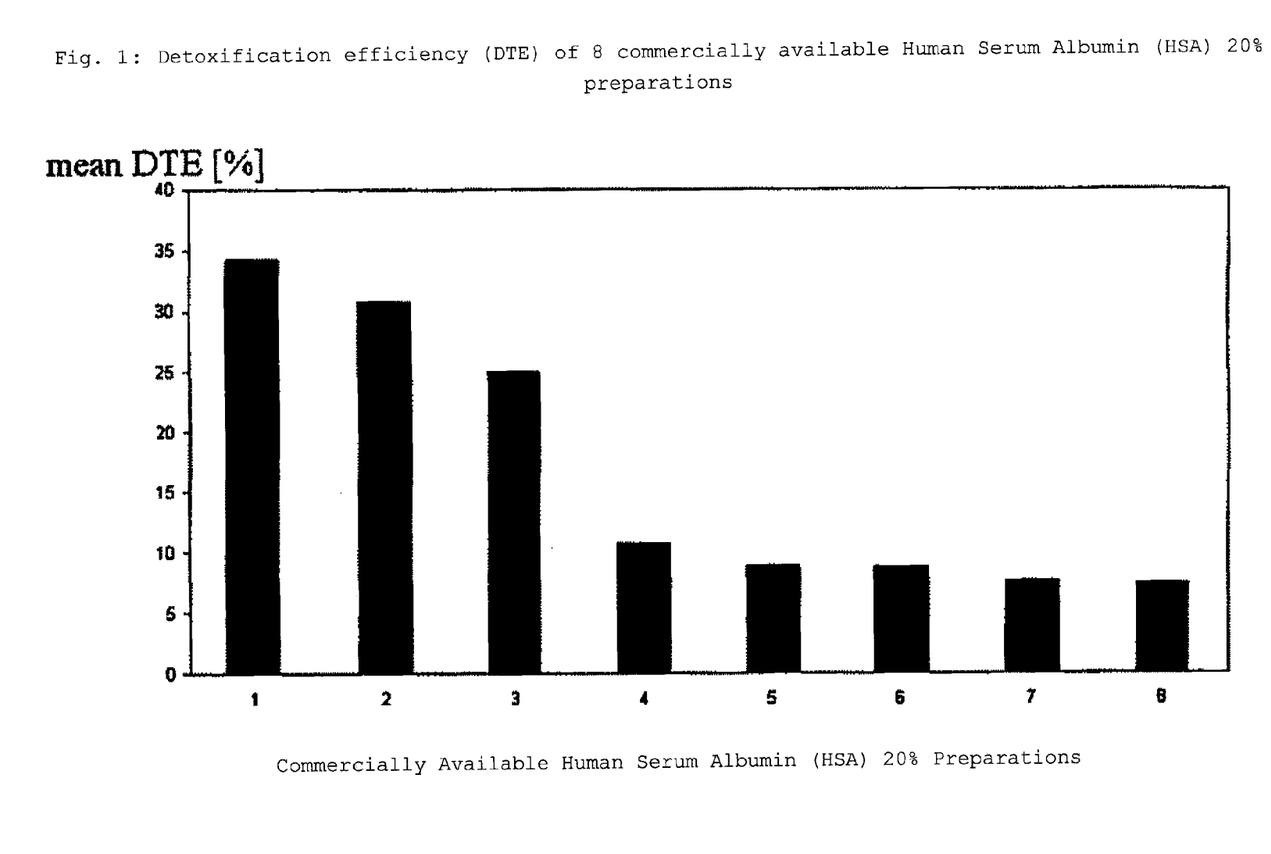
FIG. 1: Detoxification efficiency (DTE) of 8 different commercially available albumin preparations

Analysis of the Transport Parameters and Detoxification Efficiency of Commercial Albumins In a first step, 8 different commercially available albumin products were investigated by ESR for their transport properties. The results of these investigations (FIG. 1) confirmed the results of Matthes et al., 2000. The commercial albumins vary considerably in their transport quality and their detoxification efficiency (DTE), which even in the best products was only approx. 40% compared to plasma serum albumin (100%).

Example 2

Octanoate Stabilization as the Cause of the Impairment of Transport Parameters

Figure 2:
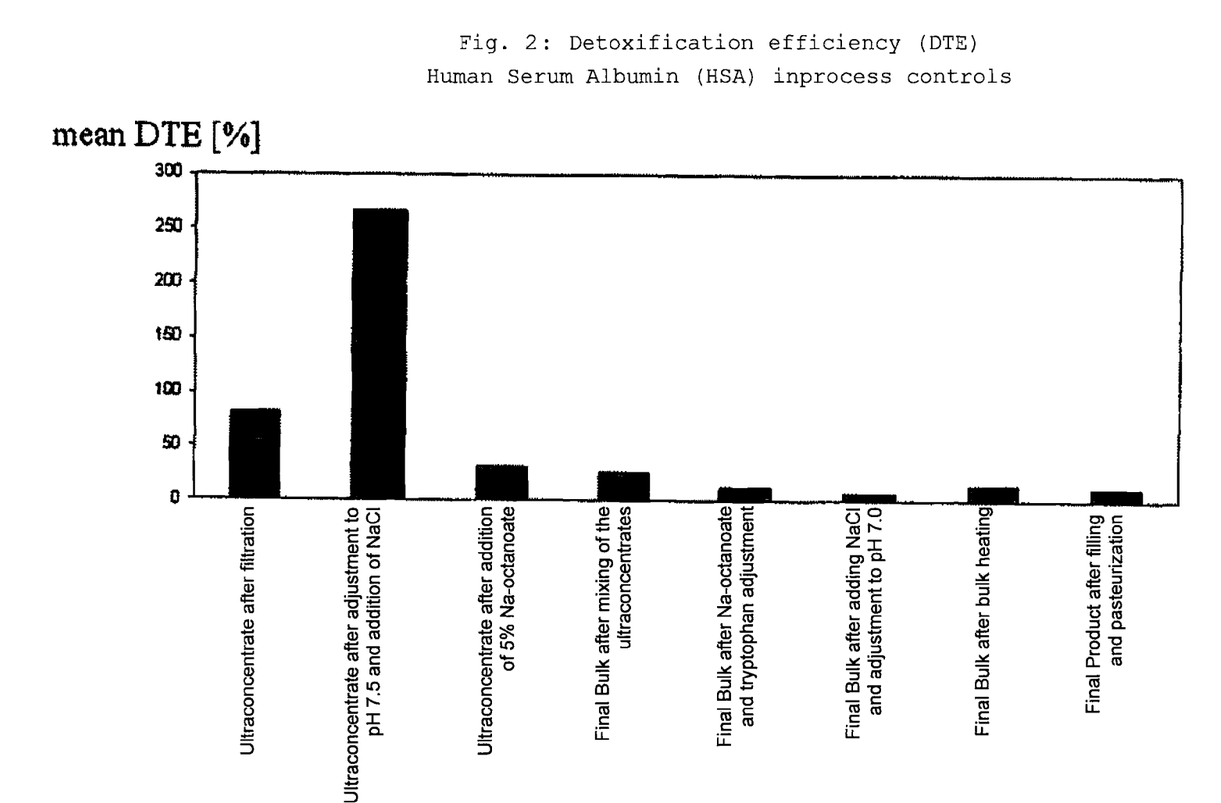
FIG. 2: Variation in detoxification efficiency (DTE) of intermediates in the production process of a commercially available albumin preparation

Intermediates in the production of a commercially available albumin preparation were investigated by ESR. Addition of 5% octanoate in step 3 of the production process and, less pronounced, adjustment to 16 mM octanoate and N-acetyl tryptophan in step 5, were identified as decisive steps in the production process that lead to a marked reduction in detoxification efficiency in comparison with normal plasma (FIG. 2).

Example 3

Production of Albumin from which Octanoate has been Removed 150 ml "Human-Albumin 20% BEHRING™", low-salt, Product No. 444 (regular commercial product) was diluted with 150 ml WFI. Then the pH was adjusted to pH 3.0 by adding 1 M hydrochloric acid. Next, 3 g activated carbon (1 g per 100 ml of diluted albumin solution) was added, stirring for 60 minutes at room temperature. The solution was filtered on a deep bed filter and a 0.2 µm membrane filter. The pH value was then adjusted to pH 7 by adding 1 M sodium hydroxide solution. The albumin solution was practically free from sodium caprylate, i.e. <95% of the original albumin-bound octanoate (analysis by gas-chromatographic determination after derivatization with DMSO (head-space chromatography)). Finally the solution was filtered on a 0.2 µm membrane filter (sterile filtration).

Example 4

Figure 3:
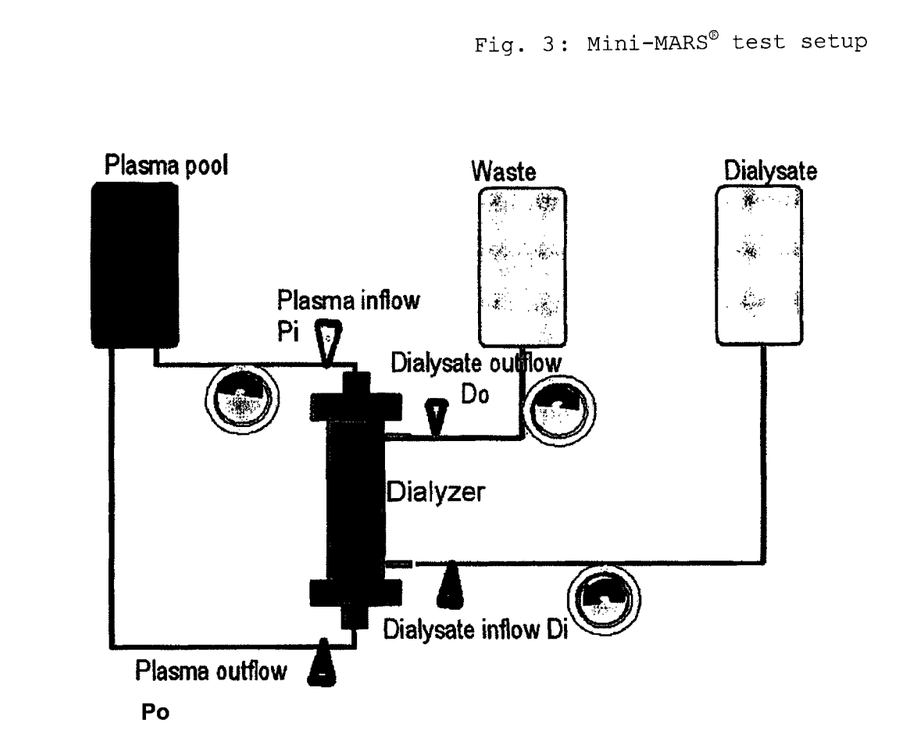
FIG. 3: Mini-MARS® experimental dialysis setup
    The dialysate containing the albumin used for detoxification flows in countercurrent to the plasma circuit.

Analysis of the Binding and Transport Properties of Octanoate-free Albumin by ESR and AbiC The albumin from which octanoate was removed according to Example 3 and products containing octanoate were investigated by ESR and AbiC (determination of albumin binding capacity with dansyl sarcosine on albumin binding site Sudlow II (Klammt S, 2000)) in an experimental dialysis setup (Mini MARS®, see FIG. 3). HSA preparations with 6.4 mM, 3.2 mM, 1.6 mM and without octanoate were used. The more octanoate was removed from the HSA, the higher the binding capacity determined in AbiC. The capacity measurements with AbiC confirmed the results of DTE measurement by ESR qualitatively (data not shown).

These HSA preparations were then dialyzed against plasma loaded with the following toxins:

10 mg/dl (127 µmol/l) bromosulfophthalein (BSP) and 20 mg/l phenytoin as binding sites II ligands and 10 mg/dl (256 µmol/l) chenodeoxycholic acid (bile acid) and 600 µg/l diazepam as binding sites I ligands were added to 1000 ml of pooled heparinized human plasma.

Figure 4:
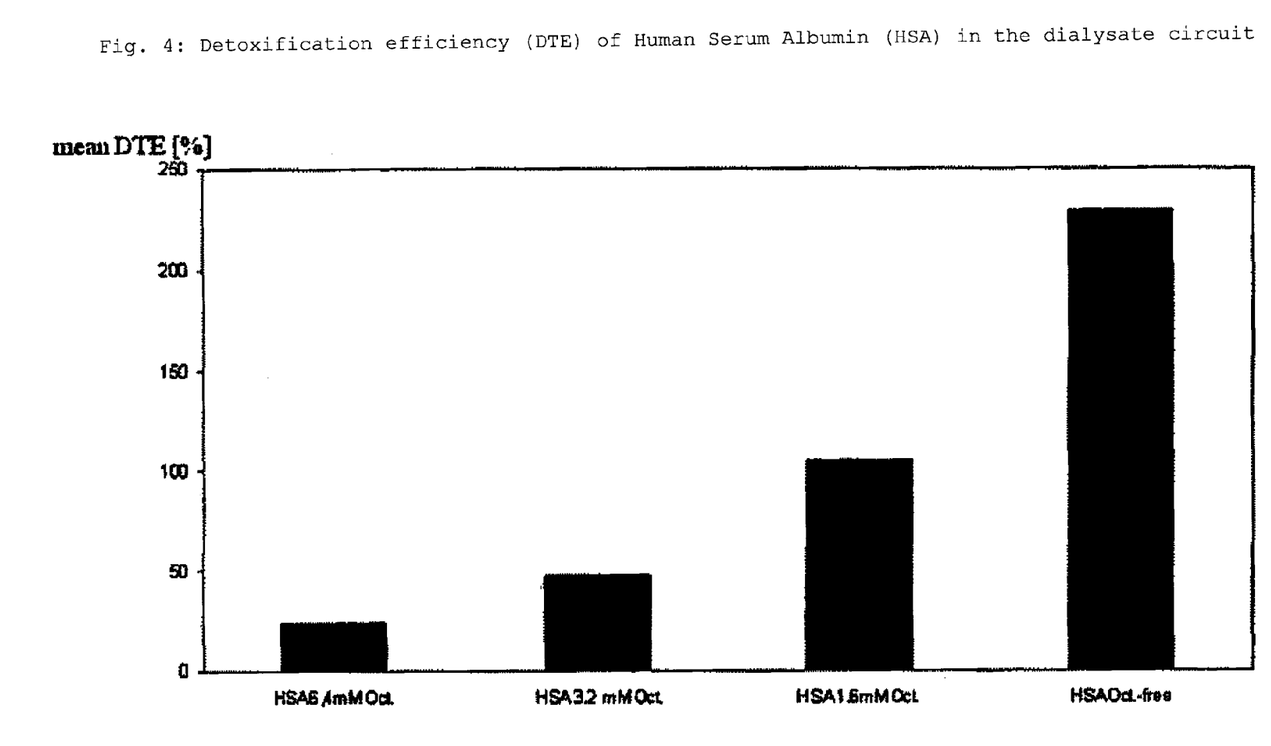
FIG. 4: Detoxification efficiency (DTE) of HSA in the dialysate circuit
    The DTE increases with decreasing octanoate content.
Figure 5:
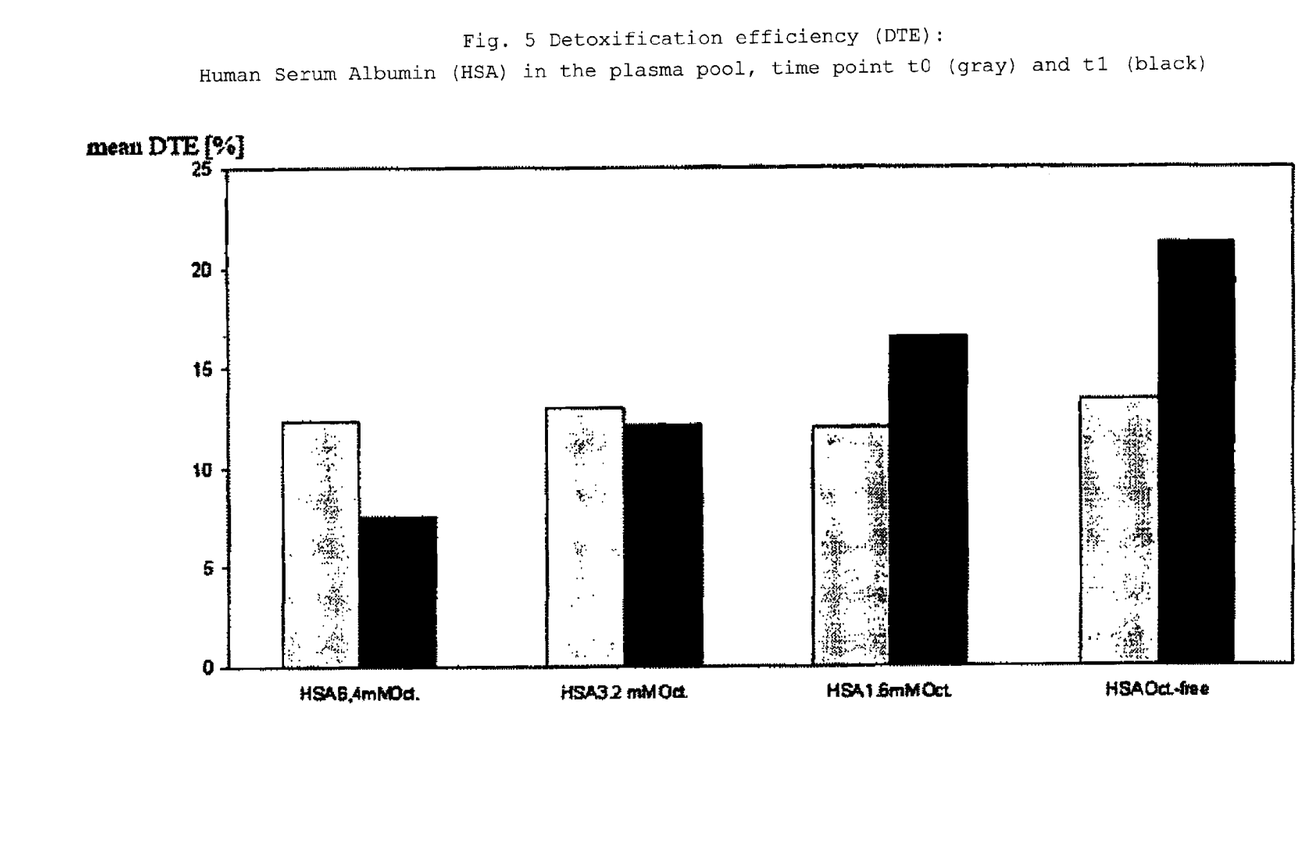
FIG. 5: Detoxification efficiency (DTE) of HSA in the plasma circuit
    The largest increase in DTE ("Detoxification of plasma albumin") occurs with octanoate-free albumin in the dialyze circuit.

The less octanoate was contained in the dialysate, the higher the DTE (FIG. 4). Furthermore, it was shown that also the DTE in the plasma could be restored by octanoate purified albumin in the dialysis circuit over time. This resulted in the largest increase in DTE of the albumin in the plasma circuit ("Detoxification of albumin" by using octanoate-free albumin in the dialysis circuit (FIG. 5)).

Example 5

Stabilization of Albumin after Removal of Octanoate

The stability of the albumin preparation after removal of octanoate according to Example 3 was investigated, after lyophilization or freeze-drying, with respect to aggregate formation according to the specifications of the European Pharmacopeia (4.0 Edition 2002), carrying out exclusion chromatography using a Toso Haas TSK™ 300 SWxl column. Aggregate formation was then calculated in accordance with the European Pharmacopeia.

| Operation | Date | % aggregate content in the lyophilizate |
| --- | --- | --- |
| Preparation of a lyophilizate from octanoate-free albumin according to Example 3 | Aug. 01, 2005 | |
| | Aug. 26, 2005 | 3.9 |
| | Oct. 06, 2005 | 3.1 |
| | Nov. 09, 2005 | 3.0 |

Thus, it could be shown that after removal of the octanoate added e.g. to prevent aggregation, stabilization with respect to aggregate formation can be achieved by freeze-drying of the octanoate-free albumin.

The invention claimed is:

1. A method for detoxifying human plasma, comprising administering extracorporeally to a patient in need thereof an amount of a pasteurized and stabilizer-reduced, but not stabilizer free, albumin preparation, wherein the amount is effective to detoxify plasma, and wherein the albumin preparation is produced by:
   (i) forming an albumin preparation by adding a sufficient amount of one or more substances that block albumin binding sites such that an adequate number of albumin binding sites are bound to inhibit albumin aggregation during pasteurization,
   (ii) pasteurizing the albumin preparation, and
   (iii) removing more than 50% of the one or more substances that block albumin binding sites after pasteurization,
   wherein aggregation stabilizers are not added to the albumin preparation after pasteurization, and
   wherein the one or more substances binding albumin comprise octanoate and/or N-acetyl-tryptophan.

2. The method of claim 1, wherein the patient suffers from liver disease.

3. The method of claim 1, wherein the patient suffers from ascites.

4. The method of claim 1, wherein the extracorporeal administration is intravenous or parenteral.

5. The method of claim 1, wherein the extracorporeal administration is by extracorporeal plasma dialysis.

6. The method of claim 5, wherein the extracorporeal plasma dialysis is molecular adsorbent recirculating system (MARS) dialysis or single-pass dialysis.

7. The method of claim 1, further comprising storing the pasteurized and stabilizer-reduced, but not stabilizer free, albumin preparation for at least three months before administration to the patient.

8. The method of claim 1, wherein production of the albumin preparation comprises removing more than 70% of the one or more substances that block albumin binding sites after pasteurization.

9. The method of claim 1, wherein production of the albumin preparation comprises removing more than 95% of the one or more substances that block albumin binding sites after pasteurization.

10. The method of claim 1, wherein the albumin preparation is a freeze-dried preparation.

11. The method of claim 10, wherein the percentage of aggregates in the albumin preparation is less than 3.9% upon reconstitution.

12. The method of claim 11, further comprising storing the pasteurized and stabilizer-reduced, but not stabilizer free, albumin preparation for at least three months before administration to the patient.

13. The method of claim 1, wherein production of the albumin preparation comprises fractionating human plasma using the Cohn process.

* * * * *